United States Patent [19]

Lin

[11] Patent Number: 5,114,899
[45] Date of Patent: May 19, 1992

[54] OLEFIN DISPROPORTIONATION CATALYST AND PROCESS

[75] Inventor: Jiang-Jen Lin, Houston, Tex.

[73] Assignee: Shell Oil Company, Houston, Tex.

[21] Appl. No.: 572,571

[22] Filed: Aug. 27, 1990

[51] Int. Cl.$^5$ ............................................... B01J 31/00
[52] U.S. Cl. ................................... 502/158; 502/300; 502/321; 502/322
[58] Field of Search ................ 502/158, 321, 322, 300

[56] References Cited

U.S. PATENT DOCUMENTS

| | | | |
|---|---|---|---|
| 3,208,985 | 9/1965 | Piekarski et al. | 502/158 |
| 3,439,057 | 4/1969 | Calderon | 260/666 |
| 3,558,518 | 1/1971 | Zuech | 252/429 |
| 3,636,126 | 1/1972 | Menapace et al. | 260/683 D |
| 3,647,906 | 3/1972 | Farley | 260/683 D |
| 3,647,908 | 3/1972 | Medema et al. | 260/683 D |
| 3,652,704 | 3/1972 | Eades et al. | 260/683 D |
| 3,671,462 | 6/1972 | O'Hara et al. | 252/429 A |
| 3,686,136 | 8/1972 | Doyle | 252/429 B |
| 3,723,563 | 3/1973 | Bradshaw | 260/683 D |
| 3,829,523 | 8/1974 | Singleton | 260/683 D |
| 3,832,417 | 8/1974 | Ruhle | 260/683 D |
| 3,940,346 | 2/1976 | Zuech | 252/430 |
| 4,266,085 | 5/1981 | Kim et al. | 585/645 |
| 4,567,159 | 1/1986 | Banks et al. | 502/158 |

FOREIGN PATENT DOCUMENTS

| | | |
|---|---|---|
| 0702726 | 1/1965 | Canada . |
| 61-125438 | 11/1984 | Japan . |
| 62-083043 | 10/1985 | Japan . |
| 6814835 | 10/1967 | Netherlands . |
| 1264973 | 6/1982 | U.S.S.R. . |
| 1002044 | 8/1965 | United Kingdom . |
| 1251854 | 11/1971 | United Kingdom . |
| 1252799 | 11/1971 | United Kingdom . |
| 1284931 | 8/1972 | United Kingdom . |

Primary Examiner—Patrick P. Garvin
Assistant Examiner—E. D. Irzinski

[57] ABSTRACT

This present invention relates to a disproportionation catalyst and a process for preparing a disproportionation catalyst comprising forming a calcined composite comprising at least one of molybdenum and rhenium supported on an inorganic oxide support and contacting the calcined composite with an organosilane compound selected from the group consisting of silanes containing at least one silicon-hydrogen bond per molecule, silanes containing at least one silicon-silicon bond per molecule and mixtures thereof, and to a process for the disporportionation of olefinic hydrocarbons comprising contacting at least one olefinic hydrocarbon with a catalyst comprising at least one of molybdenum and rhenium supported on an inorganic oxide support promoted with an organosilane compound selected from the group consisting of silanes containing at least one silicon-hydrogen bond per molecule, silanes containing at least one silicon-silicon bond per molecule and mixtures thereof.

29 Claims, No Drawings

OLEFIN DISPROPORTIONATION CATALYST AND PROCESS

FIELD OF THE INVENTION

This invention relates to a catalyst for use in the disproportionation of olefinic hydrocarbons comprising at least one of molybdenum and rhenium supported on an inorganic oxide support promoted with an organosilane compound selected from the group consisting of silanes containing at least one silicon-hydrogen bond per molecule, silanes containing at least one silicon-silicon bond per molecule and mixtures thereof and a process for the disproportionation of olefinic hydrocarbons comprising contacting at least one olefinic hydrocarbon with a catalyst comprising at least one of molybdenum and rhenium supported on an inorganic oxide support promoted with an organosilane compound selected from the group consisting of silanes containing at least one silicon-hydrogen bond per molecule, silanes containing at least one silicon-silicon bond per molecule and mixtures thereof.

BACKGROUND OF THE INVENTION

Reactions of olefinic molecules in the presence of metal-containing catalysts to produce other olefinic molecules are known in the art as "disproportionation" reactions. The olefin disproportionation reaction can be visualized as the breaking of two existing double bonds between the first and second carbon atoms, and between the third and fourth carbon atoms, respectively, and the formation of two new double bonds, such as between the first and third carbon atoms and the second and fourth carbon atoms, respectively. A typical olefin disproportionation process is illustrated by U.S. Pat. No. 3,261,879, issued Jul. 19, 1966, to Banks, wherein two similar non-symmetrical molecules of an olefin react in the presence of certain catalysts to produce one olefin of a higher carbon number and one olefin of a lower carbon number. For example, propylene disproportionates by the process of U.S. Pat. No. 3,261,879 to produce ethylene and butylenes.

A variation of this disproportionation process, which might be termed "reverse disproportionation" is illustrated by the Netherlands Patent No. 6514985 of British Petroleum Company, Limited, published May 20, 1966, wherein, in one modification, molecules of two dissimilar olefins are reacted to form two molecules of a single olefin product, e.g., ethylene and 2-butene react to form propylene.

Another variation of this process, being conveniently termed "ring opening disproportionation" to distinguish it from other variations, is disclosed by Netherlands Patent Application No. 6702703 of Phillips Petroleum Company, published Aug. 24, 1967, wherein a cyclic olefin and an acyclic olefin react to form a single product molecule. For example, ethylene reacts with cyclopentene by "ring opening disproportionation" to produce 1,6-heptadiene.

As used in this application, "disproportionation process" is meant to include all variations of disproportionations.

A variety of catalysts have been employed for conducting disproportionation reactions, such as those disclosed in U.S. Pat. No. 3,340,322, issued Sep. 5, 1967; U.S. Pat. No. 3,637,892, issued Jan. 25, 1972; U.S. Pat. No. 3,760,026, issued Sep. 18, 1973; U.S. Pat. No. 3,792,108, issued Feb. 12, 1974; U.S. Pat. No. 3,872,180, issued Mar. 18, 1975; and British Patent Specification No. 1,128,091, published Mar. 16, 1966. Among the catalysts that have been developed for disproportionation include inorganic refractory materials containing molybdenum and/or tungsten oxide.

Several patents disclose the use of promoter to enhance the disproportionation catalyst activity. Elemental metal promoters selected from the group consisting of barium, magnesium, tungsten, silicon, antimony, zinc, manganese and tin are disclosed in U.S. Pat. No. 4,568,788, issued Feb. 4, 1986, U.S. Pat. No. 4,522,936, issued Jun. 11, 1985, U.S. Pat. No. 4,524,235, issued Jun. 18, 1985 and U.S. Pat. No. 4,629,719, issued Dec. 16, 1986. In addition, organometallic compounds, such as aluminum and tin alkyls to promote solid catalysts including molybdenum and rhenium oxide for the disproportionation are disclosed in U.S. Pat. No. 4,454,368, issued Jun. 12, 1984 and U.S. Pat. No. 3,829,523, issued Aug. 13, 1974.

It is an object of this invention to provide a catalyst system with novel promoters for olefin disproportionation at high activity.

The present invention is therefore directed to a method of improving the activity of a disproportionation catalyst for converting olefins into olefins having different numbers of carbon atoms than the feed olefinic hydrocarbons.

SUMMARY OF THE INVENTION

This present invention relates to a disproportionation catalyst comprising at least one of molybdenum and rhenium supported on an inorganic oxide support promoted with an organosilane compound selected from the group consisting of silanes containing at least one silicon-hydrogen bond per molecule, silanes containing at least one silicon-silicon bond per molecule and mixtures thereof and to a process for preparing a disproportionation catalyst comprising forming a calcined composite comprising at least one of molybdenum and rhenium supported on an inorganic oxide support and contacting the calcined composite with an organosilane compound selected from the group consisting of silanes containing at least one silicon-hydrogen bond per molecule, silanes containing at least one silicon-silicon bond per molecule and mixtures thereof. The invention further relates to a process for the disproportionation of olefinic hydrocarbons comprising contacting at least one olefinic hydrocarbon with a catalyst comprising at least one of molybdenum and rhenium supported on an inorganic oxide support promoted with an organosilane compound selected from the group consisting of silanes containing at least one silicon-hydrogen bond per molecule, silanes containing at least one silicon-silicon bond per molecule and mixtures thereof.

It has been found that the activity of a disproportionation catalyst can be improved by contacting the catalyst with an organosilane compound selected from the group consisting of silanes containing at least one silicon-hydrogen bond per molecule, silanes containing at least one silicon-silicon bond per molecule and mixtures thereof, under conditions suitable for the organosilane compound to promote the activity of molybdenum and rhenium oxides. The activity of the disproportionation catalyst can be enhanced up to several orders of magnitude rate increase by the presence of an organosilane compound thus enabling the disproportionation reaction to be carried out at ambient temperature with advantages of high reaction productivity and product selectivity.

DESCRIPTION OF THE PREFERRED EMBODIMENTS

In the process of the instant invention, the disproportionation of an olefinic hydrocarbon is accomplished by contacting one or more olefinic hydrocarbons with a disproportionation catalyst comprising at least one of molybdenum and rhenium supported on an inorganic oxide support in the presence of an organosilane promoter selected from the group consisting of silanes containing at least one silicon-hydrogen bond per molecule, silanes containing at least one silicon-silicon bond per molecule and mixtures thereof.

Olefins which are suitable for disproportionation according to the instant invention are nontertiary, nonconjugated acyclic monoolefins and polyolefins having at least 2 carbon atoms per molecule including cycloalkyl, cycloalkenyl and aryl derivatives thereof; cyclic and polycyclic monoolefins and polyolefins having at least 3 carbon atoms per molecule including alkyl and aryl derivatives thereof; mixtures of the above olefins; and mixtures of ethylene and the above olefins. A useful group of olefin feed materials are acyclic olefins having carbon numbers ranging from $C_2$ to about $C_{50}$, preferably from $C_3$ to about $C_{30}$, and cyclic olefins having carbon numbers ranging from $C_4$ to about $C_{30}$. Nontertiary olefins are those olefins wherein each carbon atom, which is attached to another carbon number by means of a double bond, is also attached to at least one hydrogen atom.

Some specific examples of acyclic olefins suitable for disproportionation according to this invention are acyclic 1- and 2-alkenes, and alkyl and aryl derivatives thereof having from 2 to 30 carbon atoms per molecule. Some specific examples of such olefins are propylene, 1-butene, 2-butene, 1-pentene, 2-pentene, 1-hexene, 2-heptene, 1-octene, 2-nonene, 1-dodecene, 2-tetradecene, 1-hexadecene, 2-methyl-1-butene, 2-methyl-2-butene, 3-methyl-1-butene, 1-phenylbutene-2, 3-heptene and the like, and mixtures thereof.

Some specific examples of cyclic olefins suitable for disproportionation according to this invention are cyclobutene, cyclopentene, cycloheptene, cyclooctene, 5-n-propylcyclooctene, cyclodecene, cyclododecene, 3,3,5,5-tetramethylcyclononene, 3,4,5,6,7-pentaethylcyclodecene, 1,5-cyclooctadiene, 1,5,9-cyclododecatriene, 1,4,7,10-cyclododecatetraene, 6-methyl-6-ethylcyclooctadiene-1,4 and the like, and mixtures thereof.

The olefin feed should be essentially free of impurities which adversely affect the reaction. A subsequent reactivation of the catalyst to remove the effect of such impurities can be made repeatedly by heat treatment with air, using an inert gas to control burn-off temperature.

The disproportionation catalyst in the instant invention is prepared by forming a calcined composite comprising at least one of molybdenum and rhenium supported on an inorganic oxide support and contacting the calcined composite with a promoting amount of an organosilane compound. The inorganic oxide support comprises a solid usually containing a major proportion of silica or alumina. Such materials are commonly known as refractory oxides and include synthetic products as well as acid-treated clays or the crystalline alumina silicates known in the art as molecular sieves. Synthetic refractory oxides include silica, alumina, silica-alumina, silica-magnesia, silica-titania, alumina-titania, alumina-magnesia, boria-alumina-silica, alumina-zirconia, thoria and silica-titania-zirconia. Preferred inorganic oxide supports are alumina refractory oxides, i.e., refractory oxides containing a substantial proportion of alumina, e.g., at least about 90 percent by weight of alumina. Any conventional catalytic grade of alumina including the beta or gamma forms can be used. Generally, the inorganic oxide support has a surface area of at least 10 $m^2/g$ and preferably, the surface area is from about 25 $m^2/g$ to 800 $m^2/g$.

The molybdenum and/or rhenium can be combined with the inorganic oxide support in any conventional method such as dry mixing, ion-exchange. coprecipitation, impregnation and the like. For example, a 10–100 mesh alumina can be impregnated with an aqueous solution containing molybdenum salts, such as ammonium heptamolybdate or ammonium dimolybdate.

In a preferred embodiment, the disproportionation catalyst in the instant invention is a molybdenum oxide prepared by impregnating alumina with an aqueous molybdenum impregnation solution. The aqueous molybdenum solution consists of a water-soluble source of molybdenum oxide such as ammonium heptamolybdate or ammonium dimolybdate dissolved in water. Hydrogen peroxide may also be used to aid in solution preparation in some cases. For example, the molybdenum solution can be prepared by adding hydrogen peroxide to the solution in an amount in the range of from about 0.1 to about 1.0 mole of hydrogen peroxide per mole of molybdenum. Optionally, a suitable soluble amine compound such as monoethanolamine, propanolamine or ethylenediamine may be added to the molybdenum solution in order to aid in stabilization of the solution.

Following impregnation, the resulting material is dried and calcined. Drying is accomplished by conventional means. It may be carried out by forced draft drying, vacuum drying, air drying or similar means. Drying temperatures are not critical and depend upon the particular means utilized for drying. Drying temperatures will typically range from about 50° C. to about 150° C.

After drying, the material is calcined to produce the finished catalyst. The material may be calcined in an oxidizing or neutral atmosphere, although air is preferred. However, if binders and/or lubricants are used the material is heated in an oxygen-containing atmosphere, preferably air, in order to burn out the binders and lubricants. Calcining temperatures will typically range from about 300° C. to about 600° C. Burn-out temperatures will depend on the concentration of oxygen in the burn-out atmosphere as well as the burn-out time involved. Typically, burn-out temperatures will range from about 300° C. to about 600° C. Drying, calcining and burn-out may be combined in one or two steps. Most frequently the calcining and/or burn-out steps are combined using an oxygen-containing atmosphere.

The final calcined composites typically contain from about 1 percent by weight to about 18 percent by weight, preferably from about 5 percent by weight to about 15 percent by weight, and more preferably from about 6 percent by weight to about 12 percent by weight molybdenum and from about 1 percent by weight to about 20 percent by weight, preferably from about 5 percent by weight to about 15 percent by weight. and more preferably from about 6 percent to about 12 percent by weight rhenium. When mixtures of molybdenum and rhenium are utilized, the final catalyst typically contains from about 1 percent by weight to about 32 percent by weight molybdenum and rhenium. These types of catalysts are well known in the art and reference can be prepared according to the prior art, such as but not limited to aforementioned U.S. Pat. No. 3,261,879 and U.S. Pat. No. 3,365,513 (both of which are incorporated by reference herein) for more specific details about these types of catalysts.

The supported molybdenum and/or rhenium oxide composites are preferably subjected to a pretreatment prior to contact with the organosilane compound which is selected from the group consisting of silanes containing at least one silicon-hydrogen bond per molecule, silanes containing at least one silicon-silicon bond per molecule and mixtures thereof. While pretreatment is usually accomplished by contacting the catalyst with an oxygen-containing gas at elevated temperatures, other activation methods such as heating under a vacuum, or contact with various gases such as nitrogen or argon at high temperatures can be used. One function served by this type of pretreatment is to convert the molybdenum and/or rhenium components into the form of the oxide if these components are not initially provided in these forms. The temperature, contact times, and other conditions of pretreatment have been reported in the prior art and are generally the same conditions which are utilized to activate a disproportionation catalyst. Typically, the pretreatment conditions include a temperature in the range of from about 300° C. to about 900° C. for about 30 minutes to about 24 hours.

In order to obtain the active catalyst composition of the instant invention, the molybdenum and/or rhenium oxide supported composition is treated with an organosilane compound selected from the group consisting of silanes containing at least one silicon-hydrogen bond per molecule, silanes containing at least one silicon-silicon bond per molecule and mixtures thereof. The promoting organosilane compound can be combined with the molybdenum or rhenium oxide supported compositions in any suitable manner. For example, the molybdenum and/or rhenium oxide supported composition can be impregnated with a liquid diluent containing the organosilane compound at ambient temperature up to 150° C. After impregnation, the catalyst is then heated in an inert atmosphere, such as nitrogen or argon, to remove the liquid diluent. The temperature employed in removing the diluent and activating can vary widely; however, temperatures in the range of about 25° C. to about 200° C. are preferred. If desired, the organosilane promoter can be applied to the supported molybdenum and/or rhenium oxide in a reaction zone by spraying or otherwise contacting with the oxide. It is also contemplated that the organosilane promoter can be introduced along with the olefin feed as a means for contacting with supported molybdenum and/or rhenium oxide. In a preferred embodiment, the organosilane promoter is contacted with the supported molybdenum and/or rhenium oxide before contact with the olefin feed.

In accordance with the invention, the calcined molybdenum and/or rhenium oxide refractory materials are treated with an effective promoting amount of an organosilane compound selected from the group consisting of silanes containing at least one silicon-hydrogen bond per molecule, silanes containing at least one silicon-silicon bond per molecule and mixtures thereof and heated under conditions to form a promoted catalyst. Suitable organosilane promoters having at least one silicon-hydrogen bond per molecule include trialkylsilanes such as triethylsilane, tricyclohexylsilane, trimethylsilane, tripropylsilane, tri-n-butylsilane and tri-n-hexylsilane; mixed trialkylsilanes such as methyldiethylsilane and dimethylethylesilane; dialkylsilanes such as diethylsilane and dimethylsilane., arylsilanes such as triphenylsilane, diphenylsilane; and alkoxysilanes such as triethoxysilane. The preferred organosilane compounds having at least one silicon-hydrogen bond per molecule are trialkylsilanes such as triethylsilane, diphenylsilane, triphenylsilane, tri-n-butylsilane, and the like, with triethylsilane and diphenylsilane being especially preferred. Suitable organosilane promoters having at least one silicon-silicon bond per molecule include disilanes such as hexamethyldisilane, hexaethyldisilane and hexabutyldisilane. The preferred organosilanes having at least one silicon-silicon bond per molecule are hexamethyldislane, hexaethyldisilane, trimethyltriethyldisilane, hexaphenyldisilane and the like, with hexamethyldisilane and hexaethyldisilane being especially preferred. In a preferred embodiment, the organosilane promoter in the instant invention is a dialkyl or trialkylsilane, preferably triethylsilane, tri-n-butylsilane or diphenylsilane. Suitable molybdenum or rhenium oxide/organosilane molar ratios are typically in the range of from about 0.1 to about 500, preferably from about 1 to about 200. more preferably, from about 2 to about 100, and most preferably, from about 5 to about 50.

The disproportionation process of the invention can be carried out either batchwise or continuously, using a fixed catalyst bed, or a stirrer equipped reactor or other mobile catalyst contacting process as well as any other well known contacting technique. Preferred reaction conditions, e.g., temperature, pressure, flow rates, etc., vary somewhat depending upon the specific catalyst composition, the particular feed olefin, desired products, etc. The process is carried out at temperatures ranging from about $-10°$ C. to about 350° C. and at pressures in the range of about 50 psig to about 2000 psig. The disproportionation reaction is usually effected in a liquid phase and if desired, liquid reaction diluents are utilized. Examples of suitable diluents are hydrocarbons free from aliphatic unsaturation, such as acyclic or alicyclic alkanes of from 6 to 12 carbon atoms, i.e. hexane, isooctane and cyclohexane. Also exemplary are monoaromatic compounds such as benzene and toluene. If the diluent is added, it is present in amounts up to 20 moles of diluent per mole of olefinic reactants.

The operable range of contact time for the process of this invention depends primarily upon the operating temperature and the activity of the catalyst, which is influenced by surface area, promoter concentration, activation temperature, etc. In general, the distribution of products is not drastically altered by variation in contact time. Shorter contact times are usually associated with higher temperatures. With proper selection of conditions and contact times, very high efficiency of conversion to desired products can be obtained.

With a fixed bed reactor, continuous flow operation at pressures in the range of about 50 psig to about 2000 psig, preferably about 100 psig to about 1000 psig, with catalysts having densities ranging from about 0.3 gram per cc to about 2.0 gram per cc and surface areas greater than about 100 $m^2/g$, and at temperatures in the range of about $-10°$ C. to about 350° C., preferably at room temperature, weight hourly space velocities in the range of about 0.1 to about 10.0 parts by weight of olefinic hydrocarbon feed per part by weight of catalyst per hour are suitable. The space velocity is adjusted according to changes in density of feed due to change of pressure or temperature, and variation in reaction temperature and the activity of the catalyst.

The ranges and limitations provided in the instant specification and claims are those which are believed to particularly point out and distinctly claim the instant invention. It is, however, understood that other ranges and limitations that perform substantially the same function in substantially the same manner to obtain the same result are intended to be within the scope of the instant invention as defined by the instant specification and claims.

The process of the instant invention will be further described below by the following examples which are illustrative and which are not to be construed as limiting the invention.

ILLUSTRATIVE EMBODIMENTS

Catalyst Preparation

The disproportionation catalyst was prepared using a conventional dry pore volume impregnation technique.

A 12% $MoO_3/Al_2O_3$ catalyst was prepared as follows. A solution suitable for impregnating 88 grams of calcined alumina support with a pore volume of 1.0 cm/g was prepared as follows. An impregnation solution was made by combining 14.7 grams of ammonium heptamolybdate, 5.7 grams of 30% hydrogen peroxide and 32.4 grams of deionized water or enough water to bring the solution to a total volume of 88 milliliters. After adding the entire solution to the alumina support in several small portions with intermediate agitations, the impregnated support was dried overnight at 150° C. and calcined in air for at least 2 hours at 550° C. and in nitrogen for at least 1 hour 550° C.

A 6% $MoO_3Al_2O_3$ catalyst was prepared as follows. A solution suitable for impregnating 88 grams of calcined alumina support with a pore volume of 1.0 cm/g was prepared as follows. An impregnation solution was made by combining 7.4 grams of ammonium heptamolybdate, 2.9 grams of 30% hydrogen peroxide and 16.2 grams of deionized water or enough water to bring the solution to a total volume of 44 milliliters. After adding the entire solution to the alumina support in several small portions with intermediate agitations, the impregnated support was dried overnight at 150° C and calcined in air for at least 2 hours at 550° C. and in nitrogen for at least 1 hour at 550° C.

DISPROPORTIONATION OF 1-DECENE

EXAMPLE 1

To a 50 ml oven-dried round bottomed flask equipped with a magnetic stir bar and a three-way stopcock was added 12% molybdenum oxide on alumina catalyst (2.0 g, 1.7 mmoles $MoO_3$), 1-decene (20 mol, 105 mmoles) and triethylsilane (0.02 g, 0.17 mmoles) under nitrogen atmosphere. The mixture was then stirred at room temperature. Periodically, samples were taken and analyzed by glc. The products were further identified by gc-mass spectrometry and other analytic means. This example demonstrates high catalyst activity at room temperature for 1-decene disproportionation to $C_{18}$ olefins. The results of the disproportionation reaction are presented in Table I.

EXAMPLE 2

The disproportionation was carried out in the same manner as Example 1 except that diphenylsilane (0.008 g, 0.043 mmoles) was used in place of triethylsilane as promoter. The results of the disproportionation reaction are presented in Table I.

EXAMPLE 3

The disproportionation was carried out in the same manner as Example 1 except that diphenylsilane (0.004 g, 0.021 mmoles) was used in place of triethylsilane as promoter. The results of the disproportionation reaction are presented in Table I.

COMPARATIVE EXAMPLE A

The disproportionation was carried out in the same manner as Example 1 except that no promoter was present. The results of the disproportionation reaction are presented in Table I.

EXAMPLE 4

To a 50 ml oven-dried round bottomed flask equipped with a magnetic stir bar and a three-way stopcock was added 6% molybdenum oxide on alumina catalyst (2.0 g, 0.9 mmole $MoO_3$), 1-decene (20 mol, 105 mmoles) and diphenylsilane (0.032 g. 0.17 mmole) under nitrogen atmosphere. The mixture was then stirred at room temperature. Periodically, samples were taken and analyzed by glc. The products were further identified by gc-mass spectrometry and other analytic means. This example demonstrates high catalyst activity at room temperature for 1-decene disproportionation to $C_{18}$ olefins. The results of the disproportionation reaction are presented in Table I.

COMPARATIVE EXAMPLE B

The disproportionation was carried out in the same manner as Example 4 except that no promoter was present. The results of the disproportionation reaction are presented in Table I.

TABLE I

DISPROPORTIONATION OF 1-DECENE

| | Catalyst | Silane Added (Mmoles) | Reaction Time (hr) | Unreacted Decenes | $C_{16}=$ | $C_{17}=$ | $C_{18}=$ |
|---|---|---|---|---|---|---|---|
| Example 1 | 12% $MoO_3/Al_2O_3$ | $Et_3SiH$ (0.17) | 3 | 76 | 0 | 1 | 19 |
| | | | 18 | 43 | 0 | 2 | 48 |
| Example 2 | 12% $MoO_3/Al_2O_3$ | $Ph_2SiH_2$ (0.043) | 3 | 67 | 0 | 2 | 26 |
| | | | 18 | 22 | 2 | 11 | 48 |
| Example 3 | 12% $MoO_3/Al_2O_3$ | $Ph_2SiH_2$ (0.021) | 3 | 70 | 0 | 2 | 23 |
| | | | 18 | 21 | 2 | 11 | 49 |
| Comparative Example A | 12% $MoO_3/Al_2O_3$ | None | 3 | 79 | 0 | 0 | 3 |
| Example 4 | 6% $MoO_3/Al_2O_3$ | $Ph_2SiH_2$ | 3 | 79 | 0 | 1 | 17 |

Olefin Product Mixtures %

TABLE I-continued

| | | | Reaction | Olefin Product Mixtures % | | | |
|---|---|---|---|---|---|---|---|
| | Catalyst | Silane Added (Mmoles) | Time (hr) | Unreacted Decenes | $C_{16}=$ | $C_{17}=$ | $C_{18}=$ |
| | | (0.17) | 18 | 24 | 3 | 6 | 56 |
| Comparative Example B | 6% $MoO_3/Al_2O_3$ | None | 3 | 93 | 0 | 0 | 1 |

I claim as my invention:

1. A disproportionation catalyst comprising at least one of molybdenum and rhenium supported on an inorganic oxide support promoted with an organosilane compound selected from the group consisting of silanes containing at least one silicon-hydrogen bond per molecule, silanes containing at least one silicon-silicon bond per molecule and mixtures thereof, wherein said organoxilane compound containing at least one silicon-hydrogen bond per molecule is selected from the group consisting of triethylsilane, tricyclohexylsilane, trimethylsilane, diethylsilane, diphenylsilane, triphenylsilane, and mixtures thereof, and wherein said organosilane compound containing at least one silicon-silicon bond per molecule is selected from the group consisting of hexamethyldisilane, hexaethyldisilane, trimethyltriethyldisilane, hexaphenyldisilane, and mixtures thereof.

2. The catalyst of claim 1 wherein said organosilane compound is selected from triethylsilane and diphenylsilane.

3. The catalyst of claim 1 wherein said organosilane compound is selected from hexamethyldisilane and hexaethyldisilane.

4. The catalyst of claim 1 wherein the molybdenum and/or rhenium/organosilane molar ratio is in the range of from about 0.1 to about 500.

5. The catalyst of claim 4 wherein the molybdenum and/or rhenium/organosilane molar ratio is in the range of from about 1 to about 200.

6. The catalyst of claim 5 wherein the molybdenum and/or rhenium/organosilane molar ratio is in the range of from about 5 to about 50.

7. The catalyst of claim 1 wherein said disproportionation catalyst contains from about 1 percent by weight to about 18 percent by weight molybdenum.

8. The catalyst of claim 7 wherein said disproportionation catalyst contains from about 5 percent by weight to about 15 percent by weight molybdenum.

9. The catalyst of claim 8 wherein said disproportionation catalyst contains from about 6 percent by weight to about 12 percent by weight molybdenum.

10. The catalyst of claim 1 wherein said disproportionation catalyst contains from about 1 percent by weight to about 20 percent by weight rhenium.

11. The catalyst of claim 10 wherein said disproportionation catalyst contains from about 5 percent by weight to about 15 percent by weight rhenium.

12. The catalyst of claim 11 wherein said disproportionation catalyst contains from about 6 percent by weight to about 12 percent by weight rhenium.

13. The catalyst of claim 1 wherein said inorganic oxide support is selected from the group consisting of silica, alumina, silica-alumina, silica-magnesia, silica-titania, alumina-titania, alumina-magnesia, boria-alumina-silica, alumina-zirconia, thoria, silica-titania-zirconia and mixtures thereof.

14. The catalyst of claim 13 wherein said inorganic oxide support is alumina.

15. A process for preparing a disproportionation catalyst comprising forming a calcined composite comprising at least one of molybdenum and rhenium supported on an inorganic oxide support and contacting the calcined composite with an organosilane compound selected from the group consisting of silanes containing at least one silicon-hydrogen bond, silanes containing at least one silicon-silicon bond per molecule and mixtures thereof, wherein said organosilane compound containing at least one silicon-hydrogen bond per molecule is selected from the group consisting of triethylsilane, tricyclohexylsilane, trimethylsilane, diethylsilane, diphenylsilane, triphenylsilane, and mixtures thereof, and wherein said organosilane compound containing at least one silicon-silicon bond per molecule is selected from the group consisting of hexamethyldisilane, hexaethyldisilane, trimethyltriethyldisilane, hexaphenyldisilane, and mixtures thereof.

16. The process of claim 15 wherein said organosilane compound is selected from triethylsilane and diphenylsilane.

17. The process of claim 15 wherein said organosilane compound is selected from hexamethyldisilane and hexaethyldisilane.

18. The process of claim 15 wherein the molybdenum and/or rhenium/organosilane molar ratio is in the range of from about 0.1 to about 500.

19. The process of claim 18 wherein the molybdenum and/or rhenium/organosilane molar ratio is in the range of from about 1 to about 200.

20. The process of claim 19 wherein the molybdenum and/or rhenium/organosilane molar ratio is in the range of from about 5 to about 50.

21. The process of claim 15 wherein said disproportionation catalyst contains from about 1 percent by weight to about 18 percent by weight molybdenum.

22. The process of claim 21 wherein said disproportionation catalyst contains from about 5 percent by weight to about 15 percent by weight molybdenum.

23. The process of claim 22 wherein said disproportionation catalyst contains from about 6 percent by weight to about 12 percent by weight molybdenum.

24. The process of claim 15 wherein said disproportionation catalyst contains from about 1 percent by weight to about 20 percent by weight rhenium.

25. The process of claim 24 wherein said disproportionation catalyst contains from about 5 percent by weight to about 15 percent by weight rhenium.

26. The process of claim 25 wherein said disproportionation catalyst contains from about 6 percent by weight to about 12 percent by weight rhenium.

27. The process of claim 15 wherein said inorganic oxide support is selected from the group consisting of silica, alumina, silica-alumina, silica-magnesia, silica-titania, alumina-titania, alumina-magnesia, boria-alumina-silica, alumina-zirconia, thoria, silica-titania-zirconia and mixtures thereof.

28. The process of claim 27 wherein said inorganic oxide support is alumina.

29. The process of claim 15 wherein said composite is calcined by activating with an oxygen-containing gas at a temperature of from about 300° C. to about 800° C. prior to the addition of the organosilane promoter.

* * * * *